(12) United States Patent
Lu et al.

(10) Patent No.: US 10,113,921 B2
(45) Date of Patent: Oct. 30, 2018

(54) SYSTEMS AND METHODS FOR DETERMINING MECHANICAL STRESS OF MACHINERY

(71) Applicant: General Electric Company, Schenectady, NY (US)

(72) Inventors: Dan Tho Lu, Minden, NV (US); Pekka Tapani Sipilä, Aiglsbach (DE); Lysle Rollan Turnbeaugh, Gardnerville, NV (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 208 days.

(21) Appl. No.: 15/284,346

(22) Filed: Oct. 3, 2016

(65) Prior Publication Data

US 2017/0336274 A1    Nov. 23, 2017

Related U.S. Application Data

(60) Provisional application No. 62/339,640, filed on May 20, 2016.

(51) Int. Cl.
*G01L 1/12* (2006.01)
*G01L 9/00* (2006.01)
(Continued)

(52) U.S. Cl.
CPC .............. *G01L 1/125* (2013.01); *G01L 1/12* (2013.01); *G01L 1/127* (2013.01); *G01L 3/10* (2013.01); *G01L 3/101* (2013.01); *G01L 3/102* (2013.01); *G01L 3/103* (2013.01); *G01L 3/105* (2013.01); *G01L 3/1435* (2013.01); *G01L 9/007* (2013.01);
(Continued)

(58) Field of Classification Search
CPC ......... G01L 3/102; G01L 3/103; G01L 3/105; G01L 3/1435; G01L 3/10; G01L 3/101; G01L 1/125; G01L 1/127; G01L 1/12; G01L 9/16; G01L 9/10; G01L 9/007; G01N 2291/02863; G01N 2291/102;
(Continued)

(56) References Cited

U.S. PATENT DOCUMENTS

| 4,939,937 A | 7/1990 | Klauber et al. |
| 6,411,078 B1 * | 6/2002 | Nakagawa ........... G01R 15/183 324/117 H |

(Continued)

FOREIGN PATENT DOCUMENTS

| EP | 0 525 551 A2 | 2/1993 |
| EP | 1 400 795 A1 | 3/2004 |

OTHER PUBLICATIONS

Yoshiaki, S., et al., "Non-destructive Method of Stress Evaluation in Linepipes Using Magnetic Anisotropy Sensor", JFE Technical Report, pp. 47-53 (Jul. 2004).

(Continued)

*Primary Examiner* — Jonathan Dunlap
(74) *Attorney, Agent, or Firm* — Mintz Levin Cohn Ferris Glovsky and Popeo, P.C.

(57) ABSTRACT

Systems and methods are presented for cancelling noise from sensed magnetostriction-based strain measurements. A drive signal corresponds to a drive coil, and a sensed signal corresponds to a sensed coil. The drive signal is used to at least partially eliminate noise similar to the drive signal from the sensed signal to generate an output signal.

20 Claims, 7 Drawing Sheets

(51) Int. Cl.
 G01R 15/18 (2006.01)
 G01L 3/10 (2006.01)
 G01R 15/20 (2006.01)
 G01R 33/04 (2006.01)
 G01R 33/12 (2006.01)
 G01R 33/18 (2006.01)
 G01L 3/14 (2006.01)
 G01L 9/10 (2006.01)
 G01L 9/16 (2006.01)

(52) U.S. Cl.
 CPC .................................... *G01L 9/10* (2013.01); *G01L 9/16* (2013.01); *G01N 2291/02863* (2013.01); *G01N 2291/102* (2013.01); *G01R 15/185* (2013.01); *G01R 15/205* (2013.01); *G01R 33/04* (2013.01); *G01R 33/12* (2013.01); *G01R 33/18* (2013.01)

(58) Field of Classification Search
 CPC ........ G01R 33/18; G01R 33/04; G01R 33/12; G01R 15/185; G01R 15/205
 USPC .............. 73/862.331–862.336, 779, 862.09, 73/862.08, 760; 324/207.15, 207.2, 209, 324/207.13, 207.21
 See application file for complete search history.

(56) References Cited

U.S. PATENT DOCUMENTS

| | | | |
|---|---|---|---|
| 7,362,096 B2* | 4/2008 | Oberdier | G01D 3/036 324/209 |
| 7,658,120 B2 | 2/2010 | Asaumi et al. | |
| 9,212,958 B2* | 12/2015 | Campbell | G01L 1/125 |
| 9,429,488 B2* | 8/2016 | Lu | G01L 1/125 |
| 2007/0096724 A1* | 5/2007 | Oberdier | G01D 3/036 324/209 |
| 2014/0184210 A1* | 7/2014 | Campbell | G01L 1/122 324/209 |
| 2014/0366637 A1* | 12/2014 | Brummel | G01L 3/105 73/779 |
| 2015/0167662 A1 | 6/2015 | Hatch et al. | |
| 2015/0292962 A1* | 10/2015 | Lu | G01L 1/125 73/862.69 |

OTHER PUBLICATIONS

Extended European Search Report and Opinion issued in connection with corresponding EP Application No. 17171159.1 dated Sep. 29, 2017.

* cited by examiner

SYSTEMS AND METHODS FOR DETERMINING MECHANICAL STRESS OF MACHINERY

CROSS-REFERENCE TO RELATED APPLICATIONS

The present application claims the benefit of U.S. Provisional Application No. 62/339,640, filed May 20, 2016, entitled "SYSTEMS AND METHODS FOR DETERMINING MECHANICAL STRESS OF MACHINERY" the disclosure of which is incorporated herein by reference in its entirety and for all purposes.

BACKGROUND OF THE INVENTION

The subject matter disclosed herein relates to using magnetostriction to measure strain in industrial machinery, such as hyper reciprocating compressors.

Industrial machinery may generate stress in at least some parts of the industrial machinery. For example, hyper reciprocating compressors are used to generate high pressures in industrial settings. For example, hyper reciprocating compressors may generate pressures up to 3500 bar (50,000 psi) in compressing ethylene, polyethelene, low-density polyethylene (LDPE), or other suitable substances. In some industrial machinery, it becomes difficult to measure stress or a condition (e.g., pressure) causing the stress. Returning to the example of hyper reciprocating compressors, due to the high pressures in a hyper reciprocating compressor, it becomes difficult to measure pressures inside these hyper reciprocating compressors as traditional methods of intrusive pressure measurement are impractical. To intrusively measure the pressure inside the compressor, a hole typically must be drilled into a cylinder of the compressor, equipment passed through the hole, and the hole resealed to withstand the high pressures.

Alternatively, industrial machinery may rely on non-intrusive measurement, such as using a resistive strain gauge on a modified tie-bolt of a hyper reciprocating compressor. However, to modify and install the tie-bolt is costly and requires much time. Furthermore, when the compressors undergo maintenance, the tie-bolt might be replaced or misplaced, thereby an operator loses the ability to monitor the industrial machinery via the resistive strain gauge on the modified tie-bolt. In other machinery, a mechanical clamp-on style resistive strain gauge may be used. Although the clamp-on style resistive strain gauge may be removed at will, these gauges have a limited frequency response (dynamic strain) and often have issues with low signal-to-noise ratios (SNR), gauge creep, or the connection between the gauge and the measured component may be lost due to mechanical failure (e.g., glue fails). Accordingly, it is desirable to provide non-intrusive measurement systems and techniques that overcome the deficiencies of present systems, as described above.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a system includes a magnetostriction-based drive coil configured to generate a transitory magnetic field in a target material of industrial machinery using a drive signal. The system also includes a magnetostriction-based sensing coil configured to measure a change in magnetic permeability of the target material of the industrial machinery as a sensed signal. The system also includes noise reduction circuitry that is configured to receive the drive signal and the sensed signal. The noise reduction circuitry is also configured to at least partially remove noise in the sensed signal that corresponds to the drive signal to generate an output signal.

In a second embodiment, a method for determining strain in a portion of industrial machinery includes coupling a drive coil and a sensing coil to a target material of the industrial machinery. The target material experiences mechanical strain during operation of the industrial machinery. The method also includes generating a transitory magnetic field in a target material of industrial machinery using a drive signal via the drive coil. The method also includes measuring changes in magnetic fields using the sensing coil to generate a sensed signal as the measured change. Furthermore, the method includes at least partially reducing noise in the sensed signal using the drive signal to obtain an output signal as a change in magnetic properties of the target material.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
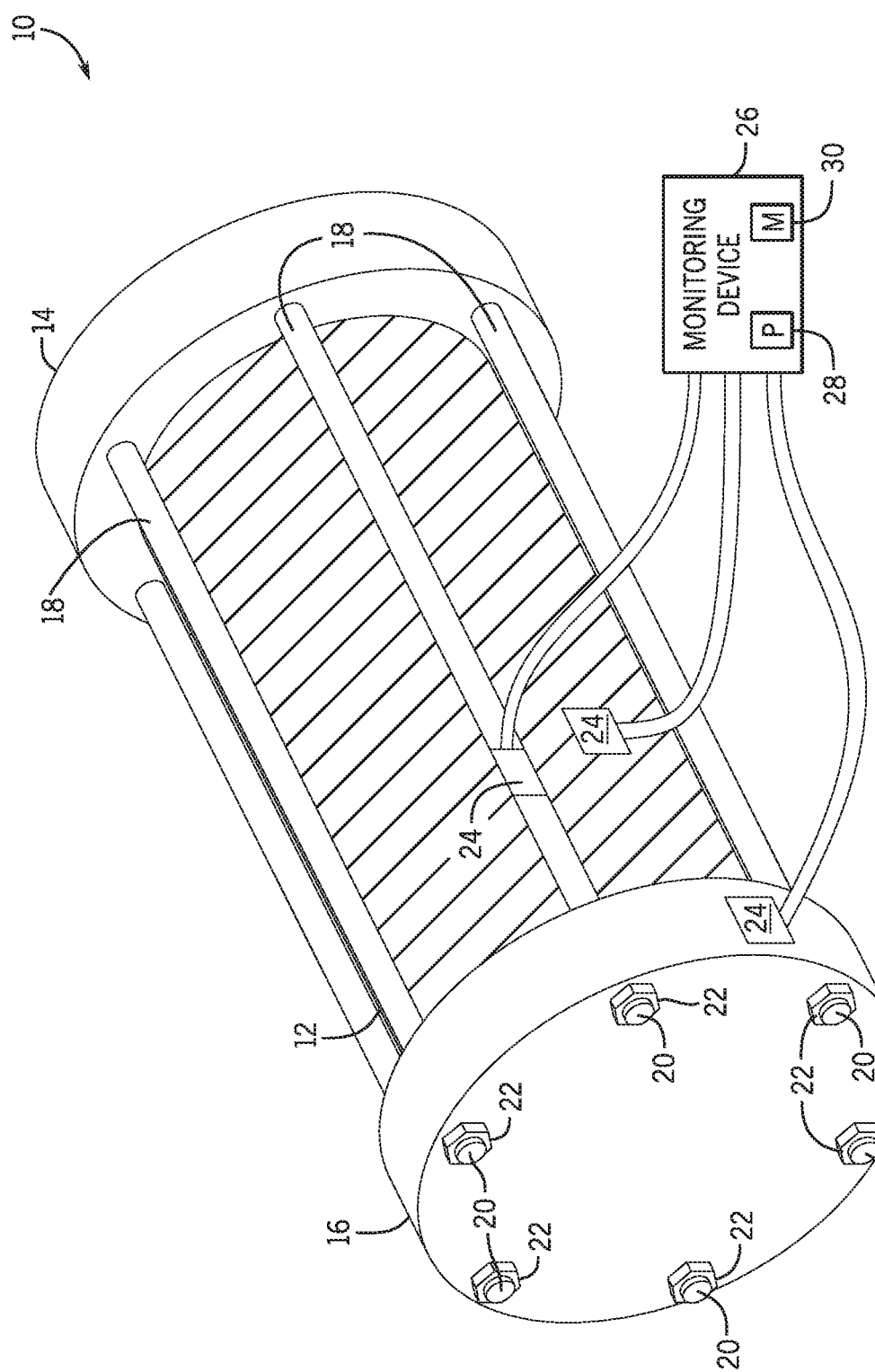
FIG. 1 is a perspective view of an embodiment of industrial machinery as a cylinder of a reciprocating compressor using a magnetostriction sensor.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

A potential method of non-invasive monitoring of pressurization within industrial machinery, such as a hypercompressor, is to measure a change in the electrical conductivity of a resistive strain gauge coupled to a target material to determine an amount of stress under which the target material is exposed. Typically, a resistive strain gauge consists of a flexible insulating backing material supporting a metallic foil pattern. The resistive strain gauge is typically attached to the target material using an adhesive, such as an adhesive from the cyanoacrylate family or some other suitable adhesive. As long as contact between the resistive strain gauge and the target material is maintained, the electric resistance of the target material can be used to determine the strain under which the target material is exposed. However, if even a portion of the strain gauge loses proper connection with the target material, the strain gauge readings may be faulty and unreliable. In other words, the resistive strain gauge requires maintenance of a direct physical connection between the resistive strain gauge and the target material else the resistive strain gauge fails.

In certain embodiments, mechanical stress of one or more portions of the industrial machinery may be determined from a magnetostriction-based sensor. By using a magnetostriction-based sensor instead of a resistive strain gauge, mechanical stress may be monitored using a contactless or indirect-contact sensor (e.g., insulated direct connection) that is less likely to lose physical connection with a material being monitored. In contrast, if a resistive strain gauge loses complete physical connection (e.g., at least partial adhesive failure) with the material being monitored, the resistive strain gauge fails. Furthermore, since the magnetostriction-based sensor may be used with a gap (e.g., filled with air or an insulating material such as paint) between the magnetostriction sensor and the target material, the magnetostriction sensor may be moved to different locations easily if the magnetostriction sensor is coupled to the target material using brackets, bolts, or braces, thus improving the quality of measured signal available for analysis.

To obtain a good mechanical adhesion and loads transfer for resistive strain gauges, anti-corrosive coating conforming to the target may have to be partially removed. This is can be time-consuming and challenging in typical application environment (e.g. if grinding tools are not allowed due to presence of explosive gasses). Also, this measurement point can be susceptible to corrosion if re-coating of the anti-corrosive layer is not done improperly. Hence, added reliability is gained with magnetostriction-based sensors, of which performance is not compromised by such anti-corrosion coatings. Furthermore, in some cases, a magnetostriction-based sensor may be capable of achieving a higher signal-to-noise ratio (SNR) and a higher frequency response than those available using resistive strain gauges.

Moreover, in general, non-contact magnetostrictive torque sensors are used with shafts that have been pre-magnetized or etched (i.e., treated). Pre-magnetization of the shaft may facilitate torque measurements by amplifying the intrinsic magnetostrictive properties of the shaft. As such, the magnetic flux generated due to the shaft torque may be detected by the non-contact magnetostrictive torque sensor. However, not all equipment or systems include pre-magnetized (e.g., treated) shafts. For example, in certain equipment, torque measurements may not have been desired at the time of manufacturing the equipment or the torque may be measured by other techniques that did not utilize magnetostrictive sensors (e.g., non-contact magnetostrictive sensors).

Retro-fitting systems with having untreated shafts with non-contact magnetostrictive sensors (e.g., if torque measurements are desired post manufacturing) may be costly and inefficient. For example, the untreated shaft may need to be removed from the equipment for treatment to generate a magnetized shaft (e.g., a treated shaft). Accordingly, shaft treatment after equipment manufacturing or after system assembly may increase labor and equipment costs associated with sensor measurements (e.g., torque) using treated shaft systems. Furthermore, in equipment that uses treated shafts (e.g., magnetized shafts), certain conditions may decrease the magnetization of the shaft (e.g., equipment overheating, impact with the shaft, etc.) over time, thereby decreasing amplification of the shaft's magnetostrictive properties, weakening the magnetic field flowing through the shaft, resulting in inaccurate torque measurements, or any combination thereof. Therefore, it may be advantageous to develop a non-contact magnetostrictive sensor that may be used with untreated (non-magnetized) rotary shafts. Non-contact magnetostrictive sensors that may be used with untreated rotary shafts may increase the accuracy of the torque measurements and facilitate retro-fitting existing systems that do not have treated shafts with a non-contact magnetostrictive sensor. In this way, equipment may be manufactured and/or retro-fit with non-contact magnetostrictive sensors for torque measurement without the costs associated with treatment (e.g., magnetization or etching) of the shaft. In addition, production efficiency for the equipment may be increased due, in part, to reducing processing steps generally associated with magnetization of the shaft.

To enable measurement of untreated shafts, the magnetostrictive torque sensor may include a driving coil to generate magnetic flux (e.g., the magnetic field) that passes through the shaft (e.g., a ferromagnetic material) and is sensed by one or more sensing coils. Changes in the measured magnetic flux depend partly on the changes in magnetic permeability of the shaft, which in turn are related to the amount of force applied to the shaft. Therefore, measurement of the magnetic flux passing through the shaft may be used to sense and/or calculate the value of the applied force (e.g., torque).

It should be pointed out that the effect of a magnetostriction-based sensor can be measured also in an in-contact-fashion electrical impedance measurements, i.e. resistance and reactance, and the changes in impedance. For example, in some embodiments, a magnetostriction-based sensor may utilize at least two electrical contacts that are located at two different locations over the measurement region. In such embodiments, the contacts may be attached to the target by mechanical clamping, welding, or soldering. By orienting the electrical contacts in different configurations, the user can sensitize the impedance measurement for detecting changes in the resistive and reactive part of the impedance due to the applied stress.

However, in some cases, magnetostriction-based sensing may have an issue with a relatively low signal-to-noise ratio (SNR), because the measured torque signal may have a relatively low amplitude when compared to a common mode signal. This is especially true when the sensing system includes some air gap (e.g., contact-less sensing). Since a magnetostriction sensor relies on magnetic flux signals to detect torque signals that appear as tension and compression stress on a detected member, the signals may be relatively low. Indeed, the nature of magnetostriction causes the torque sensor to have leakage flux that causes the sensor output signal to be very high in amplitude, but the torque signal is a relatively low portion (e.g., about 5%) of the output signal. Therefore, the signal to noise ratio is relatively low.

Thus, the following discusses using noise reduction circuitry that analyzes sensor data and subtracts at least a portion of a transmitted signal from a received signal to reduce amplitude of the common mode signals. For example, the noise reduction circuitry may include a common mode reduction circuit. The noise reduction circuitry uses a reference signal that is about the same frequency as the sensor output signal and about the same relative amplitude close to the sensor outputs. The noise reduction circuitry uses the reference signal to subtract to reduce/eliminate the non-torque-related signal from the signal. Hence, the common mode signal in the sensor may be significantly reduced. The filtered signal may be submitted to a high gain amplifier circuit to amplify the torque signal for further signal processing. As a result of the noise reduction circuitry and the amplifier, the signal to noise ratio may be substantially increased to increase accuracy in detection of stress using magnetostriction. However, if the signal is amplified prior to noise reduction, the relatively high amplitude noise may saturate a front-end analog amplifier circuit even with a relatively high voltage rail (e.g., 24V). Even if the amplifier is not saturated, the relatively large common mode signal may be too large to provide any headroom for the actual torque signal to be increased.

FIG. 1 illustrates an embodiment of industrial machinery. Specifically, FIG. 1 illustrates a portion of a hyper reciprocating compressor 10. However, the magnetostriction-based sensing discussed herein may be applied to other industrial machinery, such as turbines or other machines. The compressor 10 includes one or more cylinders 12 that reciprocate within the compressor 10 to provide pressure to pressurize a fluid (e.g., air, LDPE, etc.) within the compressor 10. Although the illustrated embodiment of the compressor 10 only illustrates a single cylinder 12, some embodiments of the compressor may include 2, 3, 4, 5, 6, or more cylinders 12. The cylinder 12 oscillates within the cylinder shaft 14 at the proximal end of the cylinder 12. At the distal end of the cylinder 12, a cylinder head 16 is coupled to the cylinder 12 using one or more tie-bolts 18. Although the currently illustrated embodiment of the compressor 10 includes six tie-bolts 18 per cylinder, some embodiments of the compressor 10 may include 1, 2, 3, 4, 5, or more tie-bolts 18 per cylinder 12. As illustrated, the tie-bolts 18 extend through the cylinder head 16 forming tie-bolt protrusions 20. In some embodiments, these tie-bolt protrusions 20 are used to fasten the cylinder head 16 to the cylinder 12. For example, in the illustrated embodiment, each tie-bolt protrusion 20 is threaded and fitted with a tie-rod nut 22. The tie-rod nuts 22 are then fastened to ensure sealed connection of the cylinder 12 with the cylinder head 16. As can be appreciated, to ensure a seal capable of withstanding the high pressures of a hyper reciprocating compressor, additional joining layers and/or joining materials may be used in the sealed connection joint between the cylinder head 16 and the cylinder 12. For example, the joint may include gaskets, sealants, or other materials/layers suitable for ensuring a sealed connection between the cylinder head 16 and the cylinder 12 under high pressures.

In a hyper reciprocating compressor, the cylinder head 16 and tie-bolts 18 oscillate with the cylinder 12 at high rates (e.g., 180 rpm) and under great pressure. Thus, mechanical stress is induced into the cylinder 12, the cylinder head 16, and the tie-bolts 18 during operation of the compressor 10. One potential method of determining the pressure within the compressor 10 is to invasively measure the pressure directly. However, this method of measurement would require creating an opening into the compressor 10 into which the pressure sensor may be inserted. Then the opening must subsequently be sealed sufficiently to withstand the high pressures within the compressor during operation. Furthermore, the presence of this sealed opening introduces an additional (and more highly susceptible) location that may fail during operation of the compressor 10 when exposed to high pressures. Instead, non-invasive methods of monitoring pressurization may be used.

Hyper reciprocating compressor 10 may include one or more magnetostriction-based sensors 24 coupled to the cylinder 12, the cylinder head 16, and/or the tie-bolts 18. Although the illustrated embodiment depicts three magnetostriction sensors 24, some embodiments may include 1, 2, 3, or more magnetostriction sensors 24 each coupled to the cylinder 12, the cylinder head 16, or the tie-bolts 18. The magnetostriction sensors 24 may be used to determine an inverse magnetostriction effect (e.g., Villari effect) of the measured material, which may include changes in magnetic permeability and magnetization of a material when subjected to mechanical stress. The magnetic permeability of a material is a proportionality constant that indicates the degree of magnetization of the material in response to an applied magnetic field. The magnitude and direction of the change depends upon the type of material being monitored. For example, when pure polycrystal iron is exposed to mechanical stress, the easy-axis of magnetization of iron turns towards the tensile direction of the stress and away from the vector orientation of the compressive stress. However, when nickel is exposed to mechanical stress, the magnetic permeability of nickel behaves oppositely.

The principal of the inverse magnetostriction effect enables the determination of stress on the measured material based on a change in the magnetic permeability or magnetization of the material from an originally measured value or an expected value for the size and composition of the material. If configurations that utilize alternating current (AC) magnetic fields are used, then changes in the magnetic permeability (or permeability) may cause changes in the induced eddy-currents over the target surface. In other words, a magnetostriction-based system may detect changes in the electromagnetic characteristics of the target material due to stress. The sensed electromagnetic characteristics can include parameters like resistivity, inductance, flux-coupling, complex magnetic reluctance, complex electrical impedance, or other electromagnetic characteristics. Furthermore, using various conversion functions or mapped conversion values, the determined strain may be extrapolated to an estimated pressure within the compressor 10.

For example, relevant information may be sent from the magnetostriction-based sensors 24 to a monitoring device 26. The transmitted information may include the magnetic permeability information, strain information determined from the magnetic permeability information, and/or the estimated pressure within the compressor 10. In other words, either the magnetostriction sensors 24 and/or the monitoring device 26 may include one or more processors 28 used to convert the magnetic permeability information into strain information determined from the magnetic permeability information, and/or the estimated pressure within the compressor 10. When the magnetostriction sensor 24 includes a processor, the processor and the magnetostriction sensor 24 share a common housing. Furthermore, in some embodiments, the monitoring device 26 may include any suitable computing device having one or more processors 28, memory 30, and/or one or more communication interfaces. The memory 30 may include non-transitory, computer-readable medium storing instructions that when executed by the one or more processors cause the processors to perform various actions. For instance, in some embodiments, the communication interfaces may include input devices (e.g., touchscreen, keypad, graphical user interface, network connections, etc.) capable of receiving input information from a user and/or a display capable of displaying the magnetic permeability information, the strain information determined from the magnetic permeability information, and/or the estimated pressure within the compressor 10.

When the magnetostriction sensors 24 are coupled to the tie-bolt 18, the magnetostriction sensors 24 determine a change in magnetic permeability of the tie-bolt 18 due to mechanical stress exerted on the tie-bolt 18 resultant from a pressure loading in the cylinder 12. Similarly, when the magnetostriction sensors 24 are coupled to the wall of the cylinder 12, the magnetostriction sensors 24 determine a change in magnetic permeability of the wall of the cylinder 12 due to mechanical stress exerted on the cylinder 12 resultant from the pressure loading in the cylinder 12. Finally, when the magnetostriction sensors 24 are coupled to the cylinder head 16, the magnetostriction sensors 24 determine a change in magnetic permeability of the cylinder head due to mechanical stress exerted on the cylinder 12 and tie-bolt 18 resultant from the pressure loading in the cylinder 12. Thus, locating the magnetostriction sensors 24 on the cylinder 12, the cylinder head 16, or the tie-bolts 18 enable measurement of a change in magnetic permeability that is proportional to the pressurization of the compressor 10.

Figure 2:
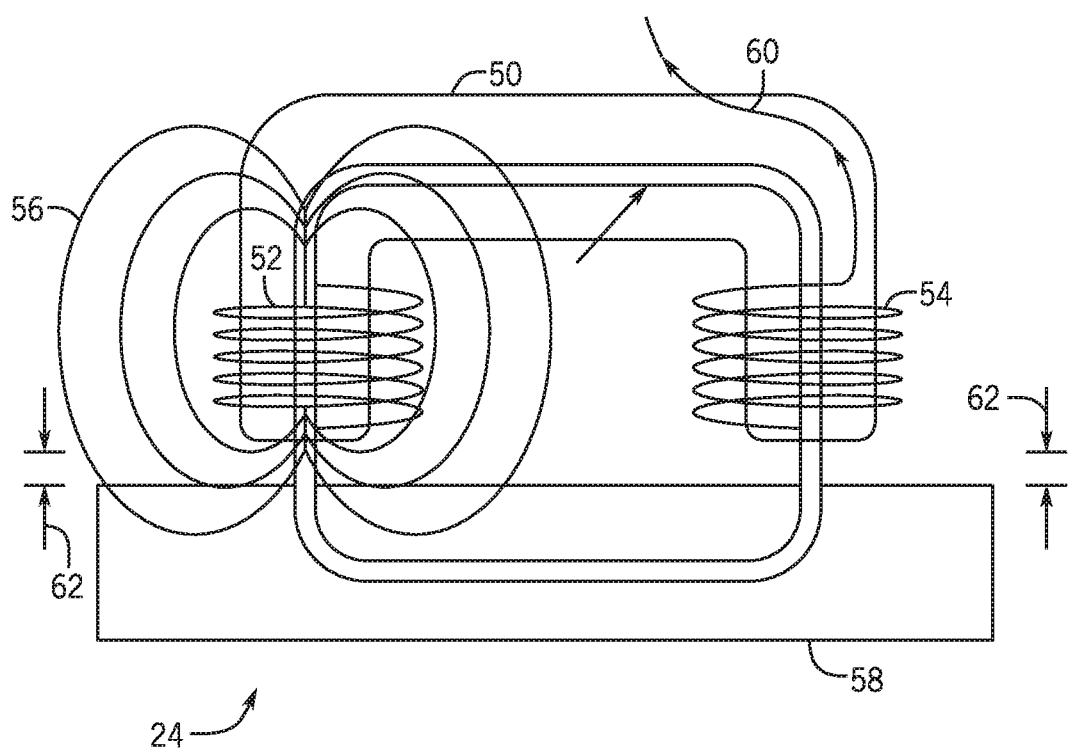
FIG. 2 is a schematic diagram of an embodiment of the magnetostriction-based sensor of FIG. 1.

FIG. 2 illustrates a first embodiment of the magnetostriction sensors 24. As previously discussed, the magnetostriction sensor 24 may be located adjacent to portions of machinery to be measured. For example, on the magnetostriction sensors may be located adjacent to the cylinder 12, the cylinder head 16, and/or the tie-bolts 18 to determine magnetic permeability fluctuations indicative of pressurization fluctuations within the compressor 10. In the illustrated embodiment, the magnetostriction sensor 24 includes a sensor core 50. In some embodiments, the sensor core 50 includes one or more processors configured to analyze measurement information, memory to store the measurement information, and/or a communication interface configured to transmit (wirelessly or physically) the measurement information (raw or analyzed) to a remote processing device (e.g., the monitoring device 26).

Additionally, the sensor core 50 provides support to a drive coil 52 and a sensing coil 54. The drive coil 52 generates a transitory magnetic field 56 using an AC and/or DC (or arbitrary pulse form) current used to create the field. When the target material 58 (e.g., the cylinder 12, the cylinder head 16, and/or the tie-bolts 18) is exposed to the magnetic field 56, the magnetic field 56 creates a secondary magnetic field (needs labeled) in the target material 58 according to the magnetic permeability of the target material 58. The secondary magnetic field 59 created in the target material 58 is then detected by the sensing coil 54 and transformed into an electrical signal 60 to be analyzed by the sensor core 50 and/or the monitoring device 26.

In some embodiments, the electrical signal 60 (raw or analyzed) is sent to the monitoring device 26 via a wired connection. In other embodiments, the electrical signal 60 is transmitted to the monitoring device 26 from the sensor core 50 using a wireless connection, such as an 805.11 connection, a WirelessHART connection, or any other suitable wireless connection.

One benefit of using a magnetostriction sensor 24 to measure strain is that the magnetostriction sensor 24 may be used to determine strain in the target material 58 using a contactless connection. This may allow for greater flexibility in placement and/or removal of the sensor 24. Thus, the magnetostriction sensor 24 may be located near the target material 58 with a gap 62 located between the magnetostriction sensor 24. In some embodiments, the magnetostriction sensor 24 may include an insulating layer between the drive coil 52/sensing coil 54 and the target material 58. In other words, the gap 62 may be at least partially filled with an insulating material and/or air. When the gap 62 is completely filled with an insulating material, the drive coil 52/sensing coil 54 maintains an indirect connection with the target material 58, because the insulating material connects the target material 58 and drive coil 52/sensing coil 54 indirectly.

In some embodiments, the gap 62 may be approximately 0.05 inches wide. In other embodiments, the gap 62 may be approximately 0.01 inches to approximately 0.5 inches, approximately 0.3 inches to approximately 0.7 inches, or more than approximately 0.7 inches wide. Thus, the contactless or indirect contact connection of the magnetostriction sensor 24 is more capable of maintaining connection between the target material 58 and the magnetostriction sensor 24 through the magnetic field 56 of the magnetostriction sensor 24 and the resultant magnetic field of the target material 58 even when the target material 58 does not physically contact the drive coil 52 or the sensing coil 54.

Figure 3:
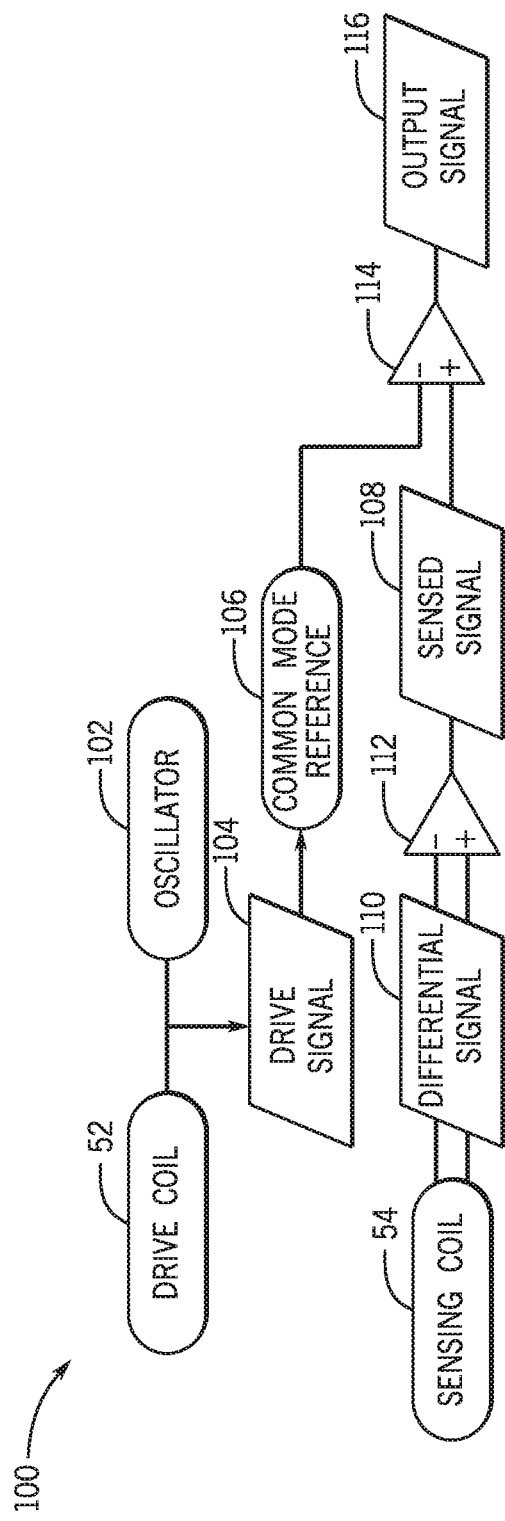
FIG. 3 is a schematic diagram of noise cancellation circuitry used to cancel noise from the magnetostriction-based sensor of FIG. 1.

FIG. 3 illustrates a noise reduction system 100 that reduces noise detected at the sensing coil 54 that corresponds to the transmission from the drive coil 52. The noise reduction system 100 includes an oscillator 102 that generates a drive signal 104 that is used to drive the drive coil 52. As noted above, the drive coil 52 uses this signal to at least partially transitorily magnetize the target material 58. This drive signal 104 may be used as a common mode reference signal 106. Additionally or alternatively, the drive signal 104, as the common mode reference signal 106, may be derived from an output of the drive coil 52. In some embodiments, the common mode reference signal 106 may be the signal sent to the drive coil 52 but with some phase and/or amplitude adjustment to enhance common mode noise cancellation. The common mode reference signal 106 is similar to a noise component in a sensed signal 108 sensed at the sensing coil 54. Moreover, the common mode reference signal 106 has a relatively high amplitude in relation to a magnetostriction component of the sensed signal 108 sensed at the sensing coil 54 but is similar in amplitude to the noise component in the sensed signal 108.

Furthermore, as illustrated, the sensed signal 108 may be derived from a differential signal 110 that is submitted to a differential amplifier 112 to obtain the sensed signal. Such differential signaling is resistant to interference.

The common mode reference signal 106 (e.g., the drive signal 104) and the sensed signal 108 are then submitted to a differential amplifier 114 that at least partially removes the noise component of the sensed signal 108 that corresponds to the common mode reference signal 106. In other words, the noise component in the sensed signal 108 that is derived from interference as direct measurement of the output from the drive signal 104 through the air rather than through the target material 58 is at least partially reduced thereby increasing the SNR for an output signal 116. The output signal 116 is proportional to and corresponds to torque (e.g., mechanical stress/strain) applied to the target material 58. The torque, in turn, may be proportional to other forces asserted on the industrial machinery. For example, the torque may be proportional to pressure inside of a hyper reciprocating compressor.

Figure 4:
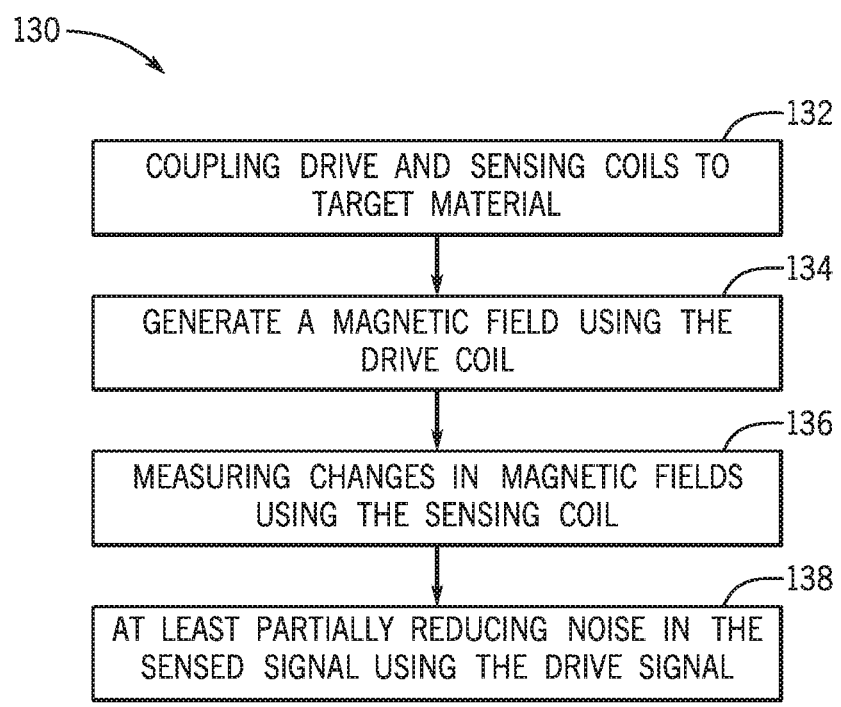
FIG. 4 is a flowchart of an embodiment of a process for reducing noise in magnetostriction-based measurements for determining mechanical stress in industrial machinery

FIG. 4 is a flowchart of an embodiment of a method 130 for determining strain of a component of industrial machinery, such as the hyper reciprocating compressor 10. In some embodiments, one or more steps of the method may be stored in the memory as non-transitory, computer-readable medium that cause a processor to perform one or more of the following steps when executed by the processor. The method 130 includes coupling a drive coil and a sensing coil to a target material of the industrial machinery, and the target material experiences mechanical strain during operation of the industrial machinery (block 132). For example, the target material may undergo mechanical strain when the industrial machinery (e.g., hyper reciprocating compressor 10) is pressurized. Moreover, the drive coil 52 and the sensing coil 54 may be coupled to the cylinder 12, the cylinder head 16, and/or the tie-bolts 18. Furthermore, the drive coil 52 and the sensing coil 54 may be coupled to the target material 58 through a connection using clamps, bolts, brackets, braces, adhesives, or other suitable coupling mechanisms. Moreover, the drive coil 52 and the sensing coil 54 may be coupled to the target material 58 using an indirect connection (e.g., through a bolt) such that the coils are located with a gap 62 between the target material 58 and the drive coil 52 and/or the sensing coil 54.

The method 130 also includes generating a transitory magnetic field in a target material 58 of industrial machinery using the drive signal 104 via the drive coil 52 (block 134). As noted above, the drive signal 104 may be the signal sent to the drive coil 52 or received directly from the drive coil 52. The sensing coil 54 measures a change in the magnetic field to generate the sensed signal 108 indicative of the measured change (block 136). As noted above, the magnetic field generated by the drive coil 52 may be inadvertently detected at the sensing coil 54, e.g. by coupling through air, causing a relatively high noise signal to overpower detection of the measured magnetic field change in the target material. Thus, the measured change at the sensing coil may have a relatively low signal-to-noise ratio (SNR). To increase the SNR, at least part of the noise is reduced in the sensed signal 108 using the drive signal 104 to obtain the output signal 116 as a change in magnetic properties of the target material 58 (block 138). The output signal 116 may be proportional to a mechanical stress in the target material 58 thereby enabling estimation of mechanical stress of the target material 58 using changes in the amplitude of output signal 116. Furthermore, reducing noise may include using noise cancellation circuitry to submit the sensed signal 108 at a positive terminal of the differential amplifier 114 and the drive signal 104 (or common mode reference signal 106) at a negative terminal of the differential amplifier 114. Thus, any common mode signal, such as the generated magnetic field at the drive coil 52, may be cancelled from the sensed signal 108 to obtain an output signal 116 with a significantly greater SNR than the sensed signal 108.

Figure 5:
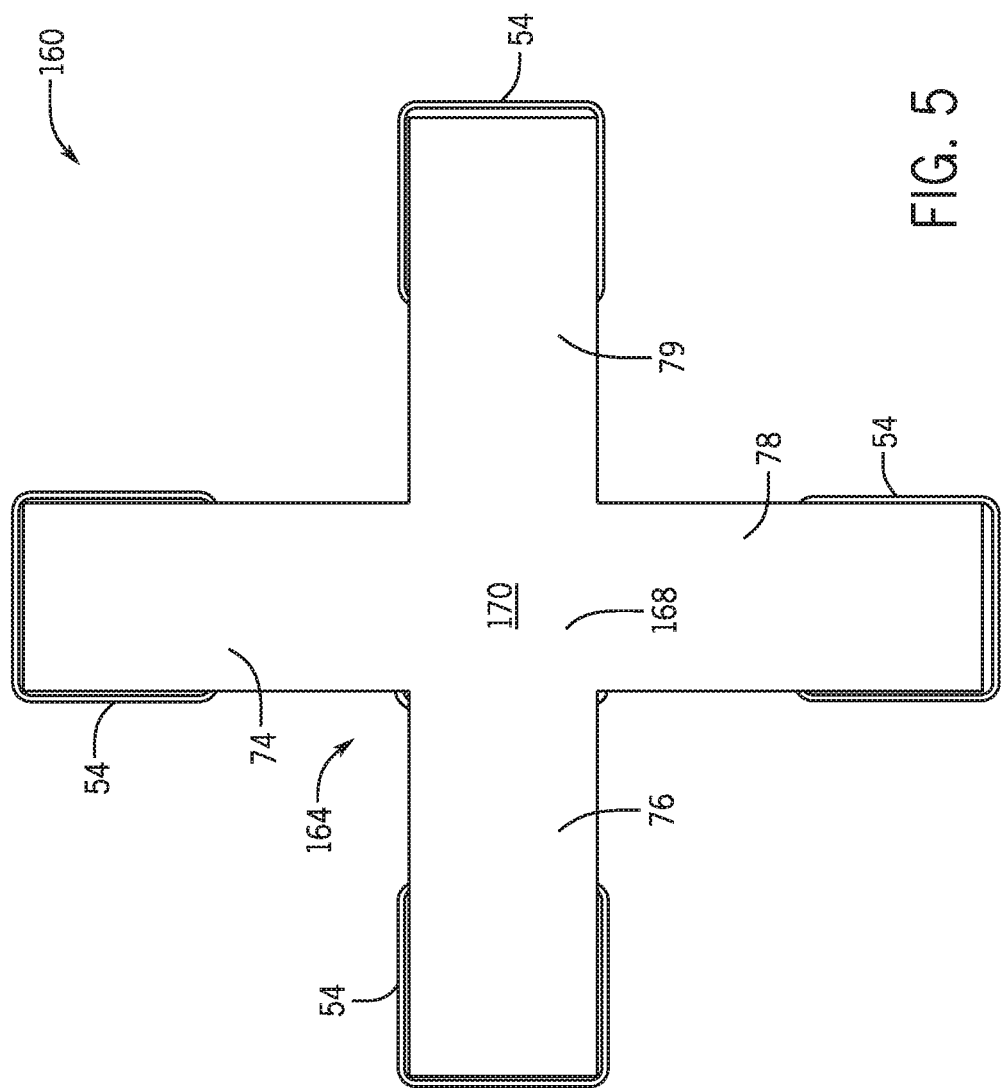
FIG. 5 is a top view of an embodiment of a sensor head of an embodiment of the magnetostriction-based sensor of FIG. 1.

FIG. 5 is a top view a sensor head 160 on a pole of an embodiment of magnetostriction sensor 24. The magnetostriction sensor 24 may be used to measure torque. The sensor head 160 includes a core 164 fabricated from any ferromagnetic material, such as iron, steel, nickel, cobalt, or other suitable magnetic material. The core 164 includes a cross axis yoke 168 with a cross yoke portion 170. Four members 174, 176, 178, and 179 of the cross axis yoke 168 extend radially outward in a plane from the yoke portion 170. The four members 174, 176, 178, and 179 are substantially orthogonal to each other around the yoke portion 170. Each of the four members 174, 176, 178, and 179 may extend from the yoke portion 170 in any configuration and for any length that enables each member to operate as described herein. In some embodiments, the yoke 168 may have any number of members, such as 1, 2, 3, 4, 5, 6, 7, 8, 9, 10, or more extending radially from the yoke portion 170. The members, such as members 174, 176, 178, and 179, may be angularly spaced apart by approximately 10, 20, 30, 40, 45, 60, 75, 90, 120, or 135 degrees, or any combination thereof. In the illustrated embodiment, the members 174, 176, 178, and 179 are angularly spaced apart by approximately 90 degrees.

Figure 6:
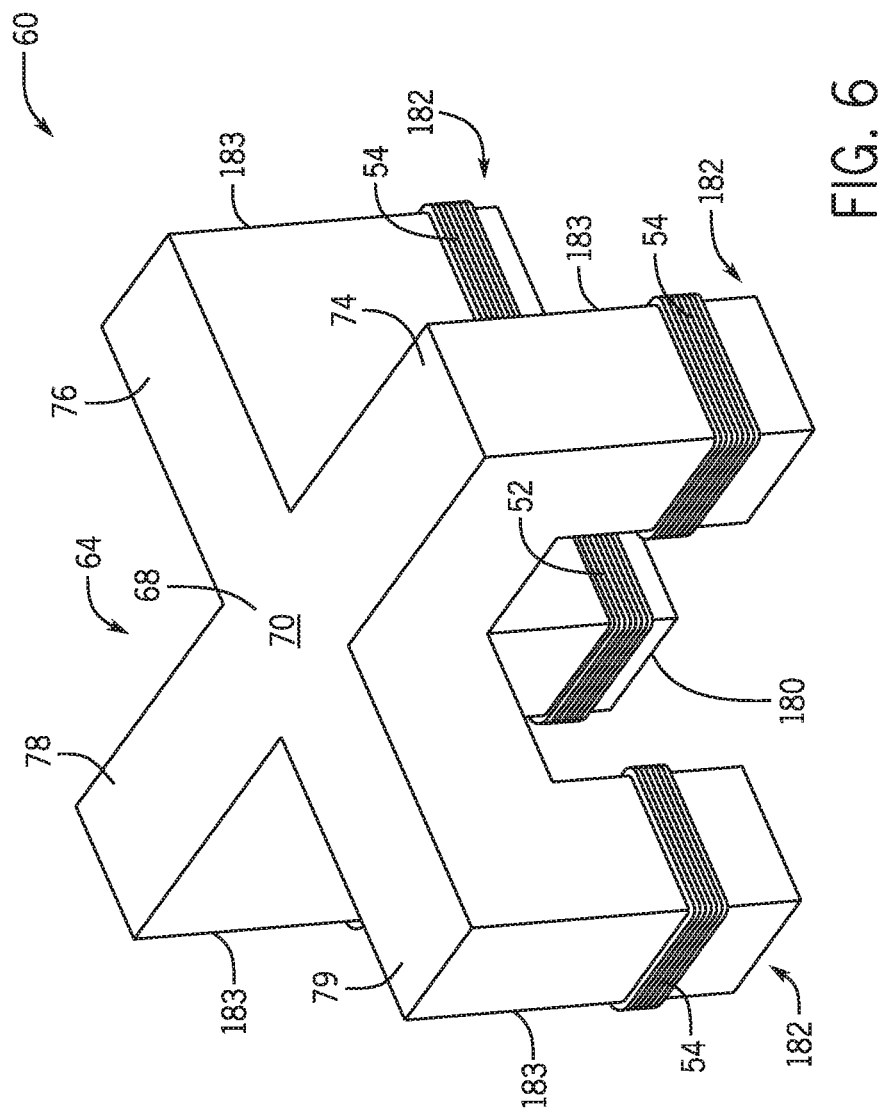
FIG. 6 is a perspective view of the sensor head of FIGS. 5.

FIG. 6 is a perspective view of the sensor head 160 illustrated in FIG. 3. As illustrated in FIG. 4, a driving pole 180 having the drive coil 52 extends outward from the yoke portion 170, perpendicular to a planar surface defined by the yoke 168. In addition, the members 174, 176, 178, and 179 extend outward from the yoke 168 substantially perpendicular to the planar surface defined by the yoke 168 and substantially parallel to driving pole 180. The sensing coils 54 extend from distal ends 182 of each respective member 174, 176, 178, and 179 at each pole 183. In certain embodiments, the poles 180 and 183 each extend an equal distance from the respective member 174, 176, 178, and 179, such that the poles 180 and 183 have the same length. To minimize variations in the gap 62 (e.g., between the target material 58 and each respective pole 180 or 183), the sensor head 160 may be rounded (e.g., dome-shaped). For example, the members 174, 176, 178, and 179 may be oriented at an acute angle (e.g., less than 90 degrees) from the planar surface defined by the yoke 168, thereby forming a rounded sensor head 160. In this way, equal-length poles 180 and 183 may follow a contour of the shaft 14, and the gap 62 between the target material 58 and each respective pole 180 and 183 is the same. In embodiments where the members 174, 176, 178, and 179 are substantially perpendicular to the planar surface defined by the yoke 168, the poles 180 and 183 may each have a variable length. The variable length for each pole 180 and 183 may facilitate maintaining a substantially constant gap 62 between the target material 58 and each respective pole 180 and 183. Therefore, similar to embodiments having a rounded sensor head, a sensor head having variable length poles 180 and 183 may follow the contour of the target material 58.

As discussed above, the driving pole 180 includes the driving coil 52 for inducing the magnetic field 56 into the target material 58. Similarly, the sensing poles 183 include sensing coils 52 wrapped around each respective member 174, 176, 178, and 179. The sensing coils 52 detect the secondary magnetic field 59 emanating from the target material 58. This sensed information may be used determine whether tension or compression forces are exerted on the target material at each pole 174, 176, 178, and 179. Specifically, tension stress increases magnetic permeability and compression reduces magnetic permeability. In other words, the change in the secondary magnetic field 59 in a negative direction may be classified as compression stress while a change in the secondary magnetic field in a positive direction may be classified as tension stress at the location of the respective pole. Furthermore, the poles 174, 176, 178, and 179 may be arranged such that adjacent poles measure opposite forces. Thus, in such embodiments, the fluctuation at two adjacent poles may be added together, if in opposite directions, to determine the torque (i.e., compression plus tension stress). Thus, the sensor head 160 of the sensor 24 may be used to determine torque exerted on the target material 58.

In operation, the sensor head 160 drives an AC current through the driving coil 52 to induce the magnetic field 56 into the target material 58, as discussed above with reference to FIGS. 1 and 2. The magnetic field 56 flows from the driving pole 180, through the target material 58 causing the secondary magnetic field 59 from the target material 58, to the four sensing poles 183, where the respective sensing coils 54 detect the secondary magnetic field 59.

Figure 7:
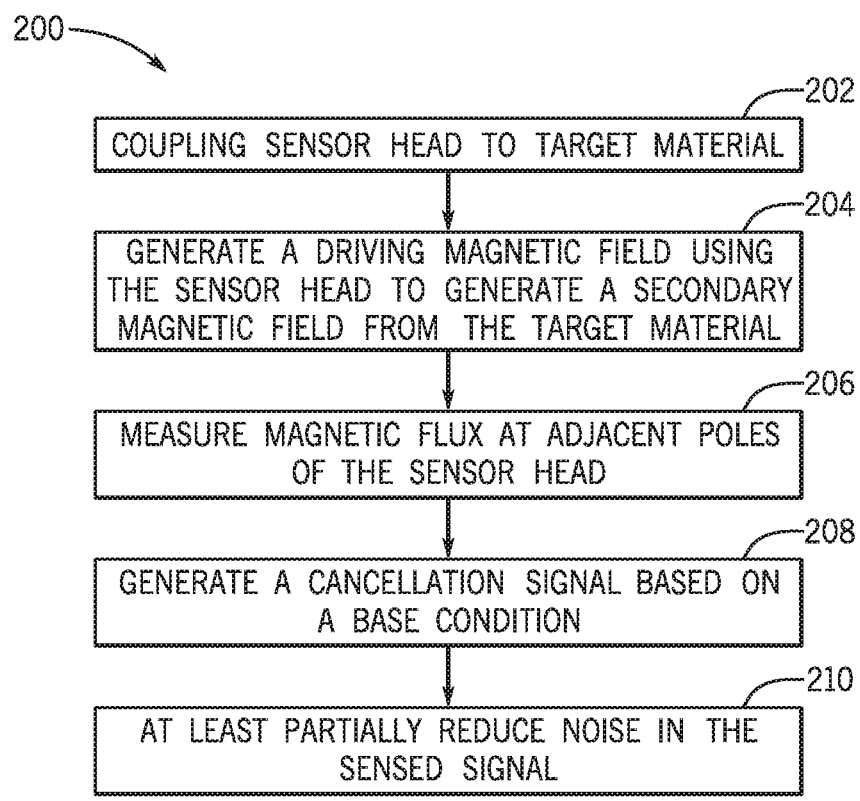
FIG. 7 is a flow diagram of a process for measuring torque using the magnetostriction-based sensor of FIG. 1.

FIG. 7 illustrates a process 200 for measuring torque using the sensor head 160. The sensor head 160 is coupled to the target material 58 (block 202). For example, the sensor head 160 may be coupled to the target material 58 using clamps, bolts, or any other suitable attachment mechanisms. The sensor head 160 is then used to generate a driving magnetic field 56 to, in turn, generate a secondary magnetic field 59 from the target material 58 (block 204). For example, the driving coil 52 may receive an alternating current (AC) current that causes the driving coil 52 to generate an AC magnetic field. The sensing coils 54 of the sensor head 160 then measure magnetic flux in the secondary magnetic field 59 (block 206). This measured magnetic flux generates a change in electric current that indicates a change in magnetic permeability based on tension or compression stress at each pole of the sensor head 160. The difference in magnetic permeability changes between adjacent sensing coils 52 may indicate an amount of torque asserted on the target material 58. However, the sensing coils 54 may also generate at least some electric current as noise due to the magnetic field 58 from the driving coil 52 directly through air. Thus, a cancellation signal (e.g., common mode reference signal 106) may be generated to cancel out the noise from the magnetic field 58 (block 208). This cancellation signal may be generated based on a driving signal for the magnetic field 59. Moreover, in some embodiments, additional fine tuning may be made to the cancellation signal to determine a baseline level for the cancellation signal at a zero torque condition based on the driving signal to determine a ratio of the drive signal to the measurement of the magnetic field 58 at the sensing coils 54. Specifically, in some embodiments, with no torque asserted on the target material 58, a measurement may be made to determine current from the sensing coils 54 that may be attributed to the driving coil 52. Indeed, in some embodiments, the zero torque measurement may be made before attaching the sensor head 160 to the target material 58. In such embodiments, any magnetic field measured at the sensing coils 54 may be attributed to the driving coil 52 (or other noise around the sensor head 160). Regardless of a method of determining the cancellation signal level, the cancellation signal may be proportional to the drive signal such that changes to the amplitude or phase of the driving signal may have a proportional change in the cancellation signal.

As previously described, using the generated cancellation signal, the noise reduction system 100 at least partially reduces noise in the signals sensed at the sensing coils 54 (block 210). As noted above, the cancellation signal uses the drive signal directly or a proportion of the drive signal to cancel measurements of magnetic fields from the driving coil 52.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system comprising:
 a magnetostriction-based drive coil configured to generate a magnetic field in a target material of industrial machinery using a drive signal;
 a magnetostriction-based sensing coil configured to measure a change in magnetic permeability of the target material of the industrial machinery as a sensed signal; and
 noise reduction circuitry configured to:
  receive the drive signal;
  receive the sensed signal; and
  at least partially remove noise in the sensed signal that corresponds to the drive signal to generate an output signal.

2. The system of claim 1, wherein the noise reduction circuitry comprises a differential amplifier that is configured to perform the at least partially removing noise by at least partially cancelling out the noise in the sensed signal using the drive signal as a noise common mode signal.

3. The system of claim 1, wherein the output signal corresponds to torque applied to the target material.

4. The system of claim 3, wherein the industrial machinery comprises a hyper reciprocating compressor.

5. The system of claim 4, wherein the torque corresponds to pressure generated in the hyper reciprocating compressor.

6. The system of claim 1 comprising a processor configured to estimate mechanical stress under which the target material is exposed based at least in part on the output signal.

7. The system of claim 1, wherein the target material comprises at least one of a cylinder wall, a cylinder head, and a tie-rod of the industrial machinery.

8. The system of claim 1, wherein the noise that corresponds to the drive signal is generated at the magnetostriction-based sensing coil when a magnetic field generated by the magnetostriction-based drive coil is sensed through air rather than through changes to the target material.

9. A method for determining strain in a portion of industrial machinery:
 coupling a drive coil and a sensing coil to a target material of the industrial machinery, wherein the target material experiences mechanical strain during operation of the industrial machinery;
 generating a magnetic field in a target material of industrial machinery using a drive signal via the drive coil;
 measuring changes in magnetic fields using the sensing coil to generate a sensed signal as the measured change; and
 at least partially reducing noise in the sensed signal using the drive signal to obtain an output signal as a change in magnetic properties of the target material.

10. The method of claim 9 comprising determining, using a processor of a monitoring system coupled to the sensing coil, an estimated mechanical stress of the target material based at least in part on the change in magnetic properties of the target material.

11. The method of claim 9, wherein at least partially reducing noise comprises:
   receiving, at noise cancellation circuitry, the drive signal;
   receiving, at the noise cancellation circuitry, the sensed signal; and
   at least partially reducing noise by submitting the drive signal and the sensed signal as inputs to a differential amplifier that reduces amplitude of noise corresponding to the drive signal in the sensed signal.

12. The method of claim 11, wherein the reduced noise and the drive signal are similar in amplitude and frequency prior to reduction.

13. The method of claim 11, wherein the noise in the sensed signal is sensed at the sensing coil by sensing a magnetic field emanating from the drive coil through air rather than a magnetic field emanating from the target material.

14. The method of claim 9, wherein the magnetic properties comprise magnetic permeability.

15. A system comprising:
   a magnetostriction-based sensor coupled to industrial machinery, wherein the magnetostriction-based sensor comprises:
      a drive coil configured to generate a magnetic field in a target material of the industrial machinery based at least in part on a drive signal; and
      a sensing coil configured to measure a change in magnetic properties of the target material of the industrial machinery as a sensed signal;
   a differential amplifier configured to:
      receive the drive signal;
      receive the sensed signal; and
      at least partially remove noise in the sensed signal that corresponds to the drive signal to generate an output signal indicative of the magnetic properties of the target material; and
   a processor configured to estimate mechanical stress based at least in part on the output signal.

16. The system of claim 15, wherein the removed noise and the drive signal are similar in amplitude and frequency.

17. The system of claim 15 comprising an insulative layer at least partially surrounding the magnetostriction-based sensor, wherein the sensing coil maintains indirect contact with the target material through the insulative layer.

18. The system of claim 17, wherein the insulative layer comprises paint.

19. The system of claim 15, wherein the magnetic property comprises magnetic permeability.

20. The system of claim 15, wherein the industrial machinery comprises a hyper reciprocating compressor.

* * * * *